United States Patent

Desai et al.

[11] Patent Number: 5,905,157
[45] Date of Patent: *May 18, 1999

[54] PROCESS FOR PRODUCING 2-(METHYLTHIO)-5-(TRIFLUOROMETHYL)-1,3,4-THIADIAZOLE USING METHYLDITHIOCARBAZINATE AND TRIFLUOROACETIC ACID

[75] Inventors: Vijay C. Desai, Shawnee; Peter E. Newallis; Vidyanatha A. Prasad, both of LeaWood, all of Kans.; Herman Seifert, Bergisch Gladbach, Germany

[73] Assignees: Bayer Corporation, Pittsburgh, Pa.; Bayer Aktiengesellschaft, Leverkusen, Germany

[ * ] Notice: This patent is subject to a terminal disclaimer.

[21] Appl. No.: 08/989,152

[22] Filed: Dec. 12, 1997

[51] Int. Cl.$^6$ .................................................. C07D 285/12
[52] U.S. Cl. ............................................................. 548/136
[58] Field of Search ............................................... 548/136

[56] References Cited

U.S. PATENT DOCUMENTS

| | | | |
|---|---|---|---|
| 3,562,284 | 2/1971 | Newman et al. | 260/302 |
| 5,101,034 | 3/1992 | Schmidt et al. | 548/136 |
| 5,147,443 | 9/1992 | Diehr et al. | 71/67 |
| 5,162,539 | 11/1992 | Diehr | 548/136 |

OTHER PUBLICATIONS

Aldrich Catalog #30,203–1 p. 1461, 1996.
Gyoefi and Csavassy, Acta Chimica Academiae Scientiarum Hungaricae, Tomus 82 (1): 91–97, 1974.

*Primary Examiner*—Robert Gerstl
*Attorney, Agent, or Firm*—Joseph C. Gil; Carol Marmo

[57] ABSTRACT

The present invention provides a process of making 2-(methylthio)-5-(trifluoromethyl)-1,3,4-thiadiazole. The process includes the steps of (a) reacting methyldithiocarbazinate with a molar excess of trifluoroacetic acid; and (b) removing the water and excess trifluoroacetic acid. Water and excess trifluoroacetic acid are preferably removed via distillation.

15 Claims, No Drawings

PROCESS FOR PRODUCING 2-(METHYLTHIO)-5-(TRIFLUOROMETHYL)-1,3,4-THIADIAZOLE USING METHYLDITHIOCARBAZINATE AND TRIFLUOROACETIC ACID

TECHNICAL FIELD OF THE INVENTION

The field of this invention is the synthesis of thiadiazoles. More particularly, this invention pertains to improved processes for making 2-(methylthio)-5-(trifluoromethyl)-1,3,4-thiadiazole using trifluoroacetic acid and methyldithiocarbazinate.

BACKGROUND OF THE INVENTION

Existing methods for preparing 2-(methylthio)-5-(trifluoromethyl)-1,3,4-thiadiazole are limited by the excessive cost of commercial scale application of laboratory procedures. Many existing reports are based on laboratory studies and thus present little information on how reaction conditions and particular reactants would affect product yield or purity. In addition, use of procedures and reactions developed in the laboratory cannot be directly applied to commercial scale production because such laboratory procedures typically involve the use of expensive reactants and/or expensive (e.g., separation and purification procedures) techniques.

U.S. Pat. No. 3,562,284 discloses a process for making certain 2-(alkylthio)-5-(halogenoalkyl)-1,3,4-thiadiazoles such as 2-(methylthio)-5-(trifluoromethyl)-1,3,4-thiadiazoles wherein methyldithiocarbazinate is reacted with a carboxylic anhydride (e.g., trifluoroacetic anhydride) or with a carboxylic acid (e.g., trifluoroacetic acid) in a solvent (e.g., toluene). The reaction can occur in the presence of phosphorous trichloride and pyridine with added sulfuric acid (DE-A-3,422,861) or with carbonyl chlorides (e.g., trifluoroacetyl chloride) and diethylene glycol dimethyl ether, as well as pyridine and sulfuric acid (DE-A-3,722,320).

The first-mentioned method is poorly suited for commercial, large-scale production because the reactants (anhydrides) are expensive and they are used in excess. In addition, by using an anhydride, only half of the reaction moiety is utilized. The reaction with carboxylic acids, phosphorus trichloride, pyridine, sulfuric acid and carbonyl chlorides requires an extensive work-up procedure in which the pyridine is separated off and recovered. Further, phosphorus trichloride forms only sparingly soluble reaction products, which makes mixing difficult and produces unacceptable amounts of waste. Finally, the yields realized from such processes are unacceptably low.

Other procedures for making a 2-(substituted)-5-(trifluoromethyl)-1,3,4-thiadiazole involve the reaction of a carboxylic acid (e.g., trifluoroacetic acid) and a dithiocarbazic ester in the presence of a phosphorylchloride or polyphosphoric acid. (See, e.g., U.S. Pat. No. 5,162,539 and Gyoefi and Csavassy, *Acta Chimica Academiae Scientiarum Hungaricae, Tomus* 82 (1): 91–97, 1974). The use of such phosphorus compounds results in the formation of waste products containing unacceptably high levels of phosphates and, thus, creates an environmental hazard. Still further, this method requires the use of dry methyldithiocarbazinates (a toxic convulsant). In the dry state this material creates a severe industrial hygiene problem.

There is a need in the art, therefore, for an efficient, high yield, practical, safe method for the commercial, large-scale production of 2-(methylthio)-5-(trifluoromethyl)-1,3,4-thiadiazole. The present invention provides such a process.

BRIEF SUMMARY OF THE INVENTION

The present invention provides a process for preparing 2-(methylthio)-5-(trifluoromethyl)-1,3,4-thiadiazole. The process includes the steps of reacting methyldithiocarbazinate in a solvent with an excess of trifluoroacetic acid with the removal of water and excess trifluoroacetic acid.

Trifluoroacetic acid is preferably present at a 10 to 500 percent molar excess relative to methyldithiocarbazinate. That is, the molar ratio of trifluoroacetic acid to methyldithiocarbazinate is from about 1.1:1 to about 5:1. More preferably, the molar ratio of trifluoroacetic acid to methyldithiocarbazinate is from about 1.25:1 to about 3.5:1 and, even more preferably from about 1.25:1 to about 2.0:1.

The reaction preferably occurs at a temperature of from about 30° C. to about 150° C. and, more preferably from about 30° C. to about 140° C. When the temperature is from about 80° C. to about 130° C., reaction time is from about 1 to about 5 hours.

The methyldithiocarbazinate used in the present process can contain up to about 50 weight percent water. The total amount of water in the reaction mixture is preferably less than about 30 grams of water per 0.5 moles of methyldithiocarbazinate.

The reaction of trifluoroacetic acid and methyldithiocarbazinate occurs in the presence of a solvent. In one embodiment, the trifluoroacetic acid serves as the solvent. Preferably, however, the solvent is an aromatic co-solvent such as toluene, xylene, cumene or mesitylene. Toluene is especially preferred.

With co-solvents, it is possible to reduce the trifluoroacetic acid quantity compared to a reaction without co-solvents. The co-solvent is present in an amount of at least about 0.5 moles of co-solvent per mole of methyldithiocarbazinate. Preferably, co-solvent is present in an amount of from about 1.5 moles to about 3.0 moles of co-solvent per mole of methyldithiocarbazinate and, more preferably in an amount of from about 2.5 moles to about 3.0 moles of co-solvent per mole of methyldithiocarbazinate.

Water is formed as a by-product in the present process. The azeotropic removal of water and excess trifluoroacetic acid is accomplished by distillation from the reaction mixture.

DETAILED DESCRIPTION OF THE INVENTION

I. The Invention

The present invention provides novel processes for preparing 2-(methylthio)-5-(trifluoromethyl)-1,3,4-thiadiazole (TDA), an intermediate useful in the preparation of herbicides. The novel processes of this invention use methyldithiocarbazinate (MDTC) and trifluoroacetic acid (TFA) as the primary reactants. The processes allow for production of TDA in high yields with efficient means for removing by-products and recycling key reagents.

II. Process Using Excess Trifluoroacetic Acid

In one aspect, a process of the present invention for preparing 2-(methylthio)-5-(trifluoromethyl)-1,3,4-thiadiazole includes the steps of reacting methyldithiocarbazinate with an excess of trifluoroacetic acid optionally in the presence of a co-solvent and removing formed water and excess trifluoroacetic acid.

MDTC prepared by any means can be used in a present process. Especially preferred means for preparing MDTC are disclosed in U.S. patent application Ser. Nos. 08/743,763, 08/743,764 and 08/743,775, all filed on Nov. 7, 1996. The disclosures of all those patent applications are incorporated herein by reference. TFA is commercially available.

TFA is preferably present at a 10 to 500 percent molar excess relative to MDTC. That is, the molar ratio of TFA to MDTC (TFA:MDTC) is from about 1.1:1 to about 5:1. More preferably, the TFA:MDTC molar ratio is from about 1.25:1 to about 3.5:1 and, even more preferably from about 1.25:1 to about 2.0:1. As shown hereinafter in the Examples, increasing the molar excess of TFA relative to MDTC increases the yield of TDA as per Table 1.

The reaction preferably occurs at a temperature of from about 30° C. to about 150° C. and, more preferably from about 30° C. to about 140° C. Reaction times depend upon the temperature. Where the temperature is from about 80° C. to about 130° C., reaction time is from about 1 to about 5 hours.

The MDTC used in the present process can contain water. The ability to use "wet" MDTC offers a substantial benefit over existing processes that use only dry MDTC. MDTC is a known toxic substance and its use in dry form is likely to result in contamination of the air in processing plants with MDTC dust. This environmental hazard is substantially reduced if wet MDTC can be used. For use in the present process, MDTC can contain up to about 50 weight percent water.

Unlike prior art processes, water may be introduced in the reaction via recycle streams. The total amount of water in the reaction mixture is preferably less than about 30 grams of water per 0.5 moles of MDTC. As shown hereinafter in the Examples, the presence of 30 or less grams of water per 0.5 moles of MDTC has no deleterious effect on product formation. Increasing the amount of water to 40 grams or more resulted in reductions of product (TDA) yield.

The reaction of TFA and MDTC occurs in the presence of a solvent. In one embodiment, the trifluoroacetic acid itself serves as the solvent. Preferably, however, an aprotic, aromatic co-solvent is used. Such co-solvents are well known in the art. Exemplary and preferred such co-solvents are toluene, xylene, cumene and mesitylene. Toluene is especially preferred.

The amount of co-solvent used can vary over a wide range as readily determined by a skilled artisan. Where a co-solvent is used, it is present in an amount of at least about 0.5 moles of co-solvent per mole of MDTC. Preferably, co-solvent is present in an amount of from about 1.5 moles to about 3.0 moles per mole of MDTC and, more preferably in an amount of from about 2.5 to about 3.0 moles of co-solvent per mole of MDTC. The reaction can proceed by mixing the entire desired amounts of MDTC and TFA. All other modes of addition are suitable as well.

The reaction mixture of MDTC and TFA can optionally include a catalyst. An example of a catalyst is p-toluenesulfonic acid, sulfuric acid, phosphoric acid, or a polyphosphoric acid. Where catalyst is used, it is present in an amount of about 2.0 grams per mole of MDTC.

Water is formed as a reaction product of the MDTC and TFA reaction. Additional water may also be present because of recycle streams. Water is removed from the reaction mixture by an azeotropic distillation. The azeotropic removal of water is readily accomplished in the presence of the solvent, particularly where toluene is used as a co-solvent. Using co-solvent, water can be removed as a separate phase from the condensate. The temperature required for the completion of the reaction is adequate for the removal of the water and excess trifluoroacetic acid via distillation. Therefore, no additional work-up is required.

The following Examples illustrate preferred embodiments of the present invention and are not limiting of the specification or claims in any way.

EXAMPLE 1

Production of 2-(methylthio)-5-(trifluoromethyl)-1,3,4-thiadiazole (TDA) Using MDTC and Excess TFA A. General Protocol Toluene (125 grams) was charged to a flask. 67.9 g (0.5 moles) of methyldithiocarbazinate (MDTC)(90% A.I. with 5% water and 5% impurities) was added to the flask to form a slurry. Trifluoroacetic acid (TFA) (114 grams, 1.0 mole) was added to the slurry with agitation over 10 to 15 minutes without cooling. The temperature of the mixture rose to about 38° C. upon TFA addition. The mixture was heated to about 70° C. and maintained at that temperature for about 3 hours. The mixture was then heated to reflux (about 115° C.–116° C.) to remove water and any distillable TFA. This temperature was maintained for about 10 minutes until no aqueous phase separates from the condensate. The yield of TDA was about 90% to 93%.

B. Effects of Excess TFA—The reaction of MDTC and TFA was carried out as set forth above in (A) except that the amount of TFA relative to MDTC was varied. TDA yields were determined at each TFA level. The results are summarized below in Table 1.

TABLE 1

Effect of TFA Excess on TDA Yield
(2.7 moles toluene/mole MDTC)

| TFA Excess, % | Net Yield, % | % Bis-By-Product (Solvent Free) |
|---|---|---|
| 0 | 70.4 | 9.8 |
| 10 | 81.5 | 9.4 |
| 20 | 88.2 | 6.2 |
| 30 | 90.2 | 5.5 |
| 40 | 91.0 | 4.3 |
| 50 | 91.1 | 3.8 |
| 100 | 92.2 | 1.9 |
| 200 | 92.8 | 1.2 |

It can be seen from the data in Table 1 that increasing the molar excess of TFA increased the yield of TDA. The greatest increases in TDA yield were seen when the molar excess of TFA increased from 10% to about 100%. Increases in the molar excess of TFA from about 100% to about 200% resulted in only small gains in TDA yield.

C. Effects of Toluene as a Solvent—TDA was prepared in accordance with (A) above except that the level of toluene relative to the level of MDTC was varied. For these studies, 2 moles of TFA were reacted with one mole of MDTC. Summary data are shown in Table 2, below.

TABLE 2

Effect of Toluene on TDA Yield
(2.0 moles TFA/mole MDTC)

| Moles Toluene/Moles MDTC | % TDA Net Yield Based on MDTC |
|---|---|
| 2.70 | 92.2 |
| 2.05 | 89.6 |
| 1.35 | 87.8 |
| 0.67 | 86.2 |

The data in Table 2 show that TDA yield increases with increasing levels of toluene. TDA yield did not improve substantially when toluene levels exceeded about 2.7 moles per mole of MDTC.

D. Effects of Water Levels—Water can be expected in the primary reaction from two main sources. First, the MDTC used in the reaction can contain water. Second, water can be added to enhance the recovery of TFA. Therefore, the effect of water on TDA recovery was studied. For these studies, 2.0 moles of TFA were reacted with one mole of MDTC. 2.1 moles of toluene per mole of MDTC were used. Results of these studies are shown below in Table 3.

TABLE 3

Effect of Water on the TDA Yield

| gms water added (0.5M batch) | TDA net yield % based on MDTC |
|---|---|
| 0 | 92.0 |
| 10 | 91.8 |
| 20 | 91.9 |
| 30 | 91.6 |
| 35 | 89.2 |
| 40 | 88.7 |
| 50 | 83.7 |

The data in Table 3 show that the presence of up to 60 grams of water per mole of MDTC in the reaction medium did not adversely affect TDA net yields. When 1.5 moles of TFA were reacted with one mole of MDTC, however, a perceptible drop in TDA net yields was noticed at water levels of 30–40 grams of water per mole of MDTC (See Table 4).

TABLE 4

Effect of Water on TDA Yield

| gms Water added (0.5M batch) | TDA net yield %* based on MDTC |
|---|---|
| 0 | 91.1 |
| 10 | 90.6 |
| 15 | 90.1 |
| 20 | 89.3 |
| 30 | 87.5 |
| 35 | 84.2 |
| 40 | 83.1 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process of making 2-(methylthio)-5-(trifluoromethyl)-1,3,4-thiadiazole comprising the steps of:

(a) reacting methyldithiocarbazinate with an excess of trifluoroacetic acid in the absence of phosphoryl chloride, wherein the molar ratio of trifluoroacetic acid to methyldithiocarbazinate is from about 1.1:1 to about 5:1 and, wherein water is a by-product of reaction; and (b) removing the water and the excess trifluoroacetic acid.

2. The process of claim 1 wherein the methyldithiocarbazinate contains up to about 50 percent by weight of water.

3. The process of claim 1 wherein the molar ratio of trifluoroacetic acid to methyldithiocarbazinate is from about 1.25:1 to about 3.5:1.

4. The process of claim 3 wherein the molar ratio of trifluoroacetic acid to methyldithiocarbazinate is from about 1.25:1 to about 2.0:1.

5. The process of claim 1 wherein the reaction occurs at a temperature of from about 30° C. to about 150° C.

6. The process of claim 5 wherein the reaction occurs at a temperature of from about 30° C. to about 140° C.

7. The process of claim 1 wherein the reaction occurs in the presence of an aprotic, aromatic solvent.

8. The process of claim 7 wherein the solvent is toluene, xylene, cumene or mesitylene.

9. The process of claim 8 wherein the solvent is toluene.

10. The process of claim 9 wherein toluene is present in an amount of at least about 0.5 moles of toluene per mole of methyldithiocarbazinate.

11. The process of claim 10 wherein the toluene is present in an amount of from about 1.5 moles of toluene per mole of methyldithiocarbazinate to about 3.0 moles of toluene per mole of methyldithiocarbazinate.

12. The process of claim 11 wherein the toluene is present in an amount of from about 2.5 moles of toluene per mole of methyldithiocarbazinate to about 3.0 moles of toluene per mole of methyldithiocarbazinate.

13. The process of claim 1 wherein water and excess trifluoroacetic acid are removed using distillation.

14. The process of claim 1 wherein water is introduced into the reaction via recycle streams.

15. The process of claim 14 wherein a total amount of the water in the reaction mixture is less than about 30 grams of the water per 0.5 moles of methyldithiocarbazinate.

* * * * *